(12) United States Patent
Behan et al.

(10) Patent No.: US 6,540,988 B1
(45) Date of Patent: Apr. 1, 2003

(54) METHOD OF REDUCING OR PREVENTING MALODOUR

(75) Inventors: John M. Behan, Kent (GB); Tony Minhas, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/743,135

(22) PCT Filed: Jul. 6, 1999

(86) PCT No.: PCT/GB99/02170

§ 371 (c)(1),
(2), (4) Date: Jan. 5, 2001

(87) PCT Pub. No.: WO00/01358

PCT Pub. Date: Jan. 13, 2000

(30) Foreign Application Priority Data

Jul. 7, 1998 (GB) .............................................. 9814646

(51) Int. Cl.⁷ .............................. A61K 7/32; A61K 7/46
(52) U.S. Cl. ........................ 424/65; 514/675; 514/724; 514/678; 514/739; 514/365; 512/1; 512/8; 512/9; 512/11; 512/13; 512/20
(58) Field of Search ........................ 424/65; 514/675, 514/724, 739, 365, 678; 512/1, 8, 9, 11, 13, 20

(56) References Cited

U.S. PATENT DOCUMENTS

| 5,260,053 A | 11/1993 | Chappell et al. | 424/65 |
| 5,554,588 A | 9/1996 | Behan et al. | 512/1 |
| 6,183,731 B1 * | 2/2001 | Carey et al. | 424/65 |

FOREIGN PATENT DOCUMENTS

| EP | 692 195 | 1/1996 |
| FR | 2 756 740 | 6/1998 |
| WO | WO 97 30689 | 8/1997 |
| WO | 9730689 | * 8/1997 |
| WO | WO 98/16194 | 4/1998 |

OTHER PUBLICATIONS

Fellahi et al: "Synthesis and antibacterial activity of 2–substituted 5–91, 2–diarylethyl)–4,6–dichloropyrimidine derivatives", European Journal of Medicinal Chemistry, Chimica Therapeutica, vol. 30, No. 7, Jan. 1, 1995, p. 633–639, XP004040189, ISSN: 0223–5234, abstract, table IV, p. 636, col. 1–col. 2.

Morris et al: "Antimicrobial Activity of Aroma Chemicals and Essential Oils", Journal of the American Oil Chemists' Society, May 1, 1979, pp. 595–603, XP000645444, ISSN:, 0003–021X, p. 595, para 1–para 3, table III.

* cited by examiner

*Primary Examiner*—Michael Williamson
(74) *Attorney, Agent, or Firm*—Morgan, Lewis & Bockius LLP

(57) ABSTRACT

A method of reducing or preventing body malodour by topically applying to human skin perfume components capable of inhibiting the production of odoriferous steroids by microorganisms on the skin. The perfume components are capable of inhibiting bacterial 4-ene reductase and/or 5α-reductase.

6 Claims, No Drawings

METHOD OF REDUCING OR PREVENTING MALODOUR

This application is the national phase of international application PCT/GB99/02170 filed Jul. 6, 1999 which designated the U.S, and that international application was published under PCT Article 21(2) in English.

This invention relates to perfume components, mixtures thereof and perfume compositions, to personal products and detergent products containing such perfumes, and to the use of such perfumes and products to deliver a deodorant effect.

In particular, it relates to perfume components, mixtures thereof, and perfume compositions for inhibiting the production of odoriferous metabolites by topically applying to human skin perfumery components capable of inhibiting the production of odoriferous steroids by micro-organisms present on the skin surface by inhibiting bacterial 4-ene reductase and/or 5α-reductase.

It is well known that freshly secreted sweat is odourless and that body malodour is the result of a biotransformation of the sweat by micro-organisms living on the surface of the skin to produce volatile odoriferous compounds.

There are three types of personal product routinely used to combat body malodour: perfumes, antiperspirants and deodorants.

Perfumes may simply mask body malodour. However perfume compositions have been disclosed which exhibit a deodorant action. EP-B-3172, EP-A-5618, U.S. Pat. Nos. 4,304,4679, 4,322,308, 4,278,658, 4,134,838, 4,288,341 and 4,289,641 all describe perfume compositions which exhibit a deodorant action when applied to human skin or when included in a laundry product used to launder textiles.

Antiperspirants work by blocking the sweat glands thereby reducing perspiration.

Antimicrobial agents used in deodorants are designed to reduce the population of micro-organisms living on the surface of the skin. Typical agents of this nature include ethanol and Triclosan (2',4,4'-trichloro-2-hydroxy-diphenyl ether) which are well known to exert antimicrobial effects. The use of common deodorant actives results in a non-selective antimicrobial action exerted upon most of the skin's natural microflora. This is an undesirable disadvantage of such deodorant formulations.

Gower et al. (J Steroid Biochem. Molec. Biol., (1994) Vol. 48, No. 4, pp 409–418) discloses the importance of certain bacterial enzymes involved in bacterial steroid metabolism in the production of odoriferous steroids.

Chen et al. (Dermatology, (1996) Vol. 193, pp 177–184) describes the importance of mammalian 5α-reductase in seborrhoea, acne, female hirsutism and androgenic alopecia. It also discusses the potential use of 5α-reductase inhibitors, in particular finasteride and turosteride in treatment of the above conditions.

Liao et al. (Biochemical and Biophysical Research Communications, (1995) Vol. 214, No. 3, pp 833–838) describes the selective inhibition of mammalian steroid 5α-reductase.

Russell and Wilson (Annual Review of Biochemistry, (1994) Vol. 63, pp 25–61) describes the moderate efficacy of polyunsaturated fatty acids in inhibiting the mammalian 5α-reductase enzymes. In particular it compares the ability of polyunsaturated fatty acids to inhibit these enzymes along with the inability of their mono-unsaturated and saturated counterparts.

U.S. Pat. No. 5,643,559 (Colgate-Palmolive Company) discloses deodorant active materials having an effective amount of $Zn"$ ions for inhibiting bacterial exoenzymes responsible for the production of axillary malodour. The bacterial exoenzymes are further characterised as aryl sulphatase or beta-glucuronidase.

DE-4343265 (Henkel) describes deodorant compositions comprising saturated dioic acid (C3–C10) esters. The active inhibits a sweat decomposing esterase and the compositions are said to not disturb the skin's natural microflora.

WO 94/07837 (Unichema) describes certain novel unsaturated dioic acids having between 8 and 22 carbon atoms. The potential use of these acids to treat malodour is also described.

Accordingly, the invention provides a cosmetic method for reducing or preventing body malodour by topically applying to human skin a composition comprising an active agent capable of inhibiting the production of odoriferous steroids by micro-organisms on the skin surface, wherein the agent is a perfume component which is capable of inhibiting bacterial 4-ene reductase and/or 5α-reductase.

The invention also provides the use of a perfume component to inhibit bacterial 4-ene reductase and/or 5α-reductase.

The invention further provides the use of a perfume composition, comprising at least 30% by weight of one or more perfume components capable of inhibiting bacterial 4-ene reductase and/or 5-reductase, to reduce body malodour.

The invention further provides the use of a deodorant product, comprising a perfume component, to reduce body malodour by inhibiting bacterial 4-ene reductase and/or 5α-reductase.

The invention further provides a perfume composition comprising at least 30% by weight of one or more of the following perfume components; (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, (2-(methyloxy)-4-propyl-1-benzenol), 4-(4-methyl-3-pentenyl)cyclohex-3-ene-1-carbaldehyde, 3-(4-methyl-3-pentenyl)cyclohex-3-ene-1-carbaldehyde, 3-(1,3-benzodioxol-5-yl)-2-methyl-propanal, α-ionone, β-ionone, 4-(4-hydroxy-4-methylpentyl)cyclohex-3-enecarbaldehyde, 3-(4-hydroxy-4-methylpentyl)-cyclohex-3-ene carbaldehyde, methyl iso-eugenol, tetrahydrolinalol, coriander, benzyl salicylate, dupical, phenyl ethyl alcohol, 9-decenol, clove leaf oil distilled, citral, vanillin, and a deodorant product comprising such a perfume composition.

The invention still further provides a method of producing a perfume composition which comprises (i) evaluating perfume components on the ability to inhibit bacterial 4-ene reductase and/or 5-reductase, (ii) selecting perfume components on the ability to inhibit bacterial 4-ene reductase and/or 5α-reductase, and (iii) mixing together two or more of said selected perfume components, optionally with other perfume components.

The term "perfume component" is used herein to represent a material which is added to a perfume to contribute to the olfactive properties of the perfume. A perfume component can be acceptably employed to provide odour contributions to the overall hedonic performance of products. Typicaily, a perfume component will be generally recognised as possessing odours in its own right, will be relatively volatile and open has a molecular weight within the range 100 to 300. Typical materials which are perfume components are described in "Perfume and Flavour Chemicals", Volumes I and II (Steffan Arctander, 1969). A perfume composition will contain a number of individual perfume components, and optionally a suitable diluent. The concentration of perfume components referred to herein is relative to the total concentration of perfume components present in the composition, ie excludes any diluent.

The cosmetic method according to the invention comprises topically applying to human skin active perfume components capable of inhibiting the production of odoriferous steroids by micro-organisms present on the skin surface. Preferably, the method reduces the production of odoriferous steroids sub-lethally. Preferably, the bacterial production of odoriferous steroids is reduced by at least 50%, more preferably by at least 70%, particularly by at least 80%, and especially by at least 90%, whilst preferably maintaining a cell viability of at least 70%, more preferably of at least 80%, and particularly of a. least 90%. The sub-lethal effect of a perfume component preferably occurs at concentrations below its minimum inhibitory concentration, determined as described in Example 1 below.

The perfume components used in the present invention are frequently incorporated into deodorant products which include, but are not limited to, body deodorants and antiperspirants including roll ons, gel products, stick deodorants, antiperspirants, shampoos, soaps, shower gels, talcum powder, hand creams, skin conditioners, sunscreens, sun tan lotions, skin and hair conditioners.

The perfume components may also be usefully employed for deodorant properties by incorporation into other products, for example, in to laundry and household products such as rinse conditioners, household cleaners and detergent cleaners. The perfume components can be incorporated into textiles themselves during their production using techniques known in the art, to provide deodorant protection.

It has been shown that the bacterial production of odoriferous steroids can be reduced or eliminated without significantly disturbing the skin's natural microflora. This is achieved by inhibiting bacterial enzymes responsible for the production of odoriferous steroids, in particular the 16-androstenes.

It has also been shown that many inhibitors of mammalian 5α-reductase, e.g. finasteride, are incapable of sub-lethally inhibiting the bacterial production of odoriferous steroids.

The odoriferous steroids which are inhibited by the method of the invention include the products or intermediates of bacterial steroid metabolism, in particular the 16 androstenes.

In a preferred method according to the invention, an Odour Reduction Value, measured as described in Example 3, of at least 10%, more preferably a; least 30%, and particularly at least 50% is obtained. The active perfume components may be mixed with other perfume components to deliver perfumes or perfume compositions with the desired deodorant and hedonistic properties. To deliver high deodorant effects the active components preferably comprise 30% or more of the total perfume formulation by weight, more preferably at least 40% and particularly at least 60%. A deodorant product preferably comprises at least 0.05% to 4%, more preferably 0.1% to 2% by weight of the active perfume components. Preferred actives include the following perfume components.

(Z)-3,4,5,6,6-pentamethylhept-3-en-2-one (Acetyl di iso amylene)
Mixtures of diethyl- and dimethyl-cyclohex-2-en-1-one (Azarbre)
Citronellol
2-methyl-3-(4-(1-methylethyl)phenyl)propanal (Cyclamen aldehyde)
(2-(methyloxy)-4-propyl-1-benzenol) (Dihydroeugenol)
4-(4-methyl-3-pentenyl)cyclohex-3-ene-1-carbaldehyde (Empetaal)
3-(4-methyl-3-pentenyl)cyclohex-3-ene-1-carbaldehyde (Empetaal)
3-(1,3-benzodioxol-5-yl)-2-methylpropanal (Helional)
α-ionone, β-ionone and mixtures thereof (Ionone)
4-(4-hydroxy-4-methylpentyl)cyclohex-3-enecarbaldehyde (Lyral)
3-(4-hydroxy-4-methylpentyl)cyclohex-3-enecarbaldehyde (Lyral)
Methyl iso-eugenol
Tetrahydrolinalol
Coriander
Benzyl Salicylate
Dupical
Phenyl Ethyl Alcohol
9-Decenol
Clove Leaf Oil Distilled
Citral
Vanillin.

A perfume composition for use in the present invention preferably comprises at least 5, more preferably at least 10, and particularly at least 15 of the above perfume components.

The invention is illustrated by the following examples.

EXAMPLE 1

The minimum inhibitory concentration of perfume components was determined by the following method.

A fresh culture of of the test inoculum (Corynebacteria xerosis NCTC 7243 (National Collection of Type Cultures, Public Health Laboratory Service, Central Public Health Laboratory, 61 Colindale Avenue, London)) diluted in sterile 0.1% special peptone solution to give a concentration of approximately $10^6$ cfu/ml was prepared.

Test samples were diluted in sterile trptone soya broth (TSB) Each row of the microtitre plate (labelled A–H) was allocated to one sample, i.e. eight samples per plate. Row 8 (H) contained only TSB for use as a bacterial control to indicate level of turbidity in the absence of test material. Aseptically 200 μl of the initial dilution was transferred to the 1st and 7th well of the appropriate row. All other test wells were filled with 100 μl of sterile TSB using an 8 channel pipette. The contents of all wells in column 1 were mixed by sucking samples up and down pipette tips before 100 μl was transferred to column 2. The same sterile pipette tips can be used to transfer 100 μl of each well in column 7 in to the appropriate well in column 8. Tips were discarded into disinfectant solution. Using fresh sterile tips the process was repeated by transferring 100 μl from column 2 into column 3 (and 8 into 9). The process was continued until all wells in columns 6 and 12 contained 200 μl. After mixing 100 μl was discarded from wells in these columns to waste.

To all wells 100 μl of pre-diluted test culture was added giving 200 μl final volume in each well.

A blank plate was prepared for each set of samples using the above protocol except 100 μl of sterile 0.1% peptone was added instead of bacterial culture.

Plates were sealed using autoclave tape and incubated overnight at 35° C.

The reader was preset to gently agitate the plates to mix the contents before reading absorbance at 540 nm. The control plate for each set of samples was read first. The reader was then reprogrammed to use the control readings to blank all other plate readings of the set of test materials (i.e. removing turbidity due to perfume and possible colour changes during incubation) thus only printing out absorbances due to turbidity resulting from bacterial growth. Limits were set so that degrees of turbidity were given a rating.

The MIC was taken as the level of sample required to inhibit growth completely (change in absorbance<0.2).

EXAMPLE 2

The ability of perfume components to inhibit the bacterial 4-ene reductase enzyme was determined in vitro using the conditions given below. The perfume components were tested at a range of concentrations (eg 500 ppm and 1000 ppm) below their predetermined minimum inhibitory concentration.

The experiments were carried out in sterile glass screw capped vials containing a suspension (1 ml) of an ungrouped coryneform species deposited as NCIMB 13589 (deposited under the Budapest Treaty with National Collections of Industrial and Marine Bacteria Ltd, 23 St Machar Drive, Aberdeen Scotland, UK on Jun. 28, 1999), isolated from human underarm samples capable of mediating the reduction of the unsaturated double bond at position 4 of an unsatuirated steroid molecule. This was prepared from a 24 h culture of bacteria grown in growth medium, washed in potassium phosphate buffer (50 mM, pH 6.0), and resuspended in biotransformation medium, as described below. Active-emulsion and substrate (androstadienone 50 μg/assay) were added to the bacterial suspension and experimental samples incubated over 24 h at 35° C. with agitation (100 rpm). Biotransformation of androstadienone to androstenone was measured by capillary GC-MS analysis of the cultures following solvent extraction (Folch et al., J. Biol. Chem. 226: 498–509) with an internal standard, androsterone. Enzyme inactivation of bacterial 4-ene reductase was measured by capillary GC-MS using a Hewlett Packard 5972 MSD GC-MS fitted with a 30 m×0.32 mm HP-5 fused silica capillary column (0.25 μm film thickness) and helium carrier gas. The injection temperature was 80° C., which was held for 1 min, then increased to 200° C. at 10° C./min, then to 300° C./min, at 20° C./min, with the final iso time of 10 min. Androstenone was identified from fragmentation patterns and standards, and levels in the biotransformation samples were determined using the internal standard and calibration curves of androstenone.

Growth media used for the preparation of the bacterial inoculum was composed of 200 ml of tryptone soya broth (20 g/l), yeast extract (10 g/l), and Tween 80 (2.5 g/l). Biotransformation was carried out in the medium published previously (Kawahara, F. S. (1969) Meths. Enzymol. V, 527–532). In addition it is possibie to carry out this reaction in medium (TSBT) defined by Gower et al, Journal of Steroid Biochemistry and Molecular Biology, Vol. 48, No. 4, pp 409–418. The active emulsion was prepared using potassium phosphate buffer (50 mM, pH 6.0), supplemented with Triton X 100 (5 g/l).

EXAMPLE 3

The following are typical formulations of deodorant products which comprise a perfume or perfume component capable of inhibiting the production of odoriferous steroids. These formulations are made by methods common in the art.

Deodorant Sticks

| Ingredient | Content (% by weight) | |
|---|---|---|
| | Formulation 1A | Formulation 1B |
| Ethanol | | 8.0 |
| Sodium Stearate | 7.0 | 6.0 |
| Propylene glycol | 70.0 | 12.0 |
| Perfume | 1.5 | 2.0 |
| PPG-3 Myristyl ether | | 28.0 |
| PPG-10 Cetyl ether | | 10.0 |
| Cyclomethicone | | 34.0 |
| Silica | | |
| Water | 21.5 | |

Aerosols

| Ingredient | content % by weight | |
|---|---|---|
| | Formulation 2A | Formulation 2B |
| Ethanol B | up to 100 | |
| Propylene glycol | as required | |
| Perfume | 2.5 | 1.5 |
| Chlorhydrol microdry | | 31.8 |
| Silicone Fluid DC344 | | up to 100 |
| Bentone gel IPP | | 13.65 |
| Irgasan DP300 | 0.03 | |
| Dimethyl ether | 20.0 | |
| Concentrate | | 22.0 |
| Water | 23.0 | |

Roll ons

| Ingredient | Content % by weight | |
|---|---|---|
| | Formulation 3A | Formulation 3B |
| Ethanol | to 100% | 60.0 |
| Klucel MF | | 0.65 |
| Cremphor RM410 | | 0.5 |
| Perfume | 0.5 | 1.0 |
| AZTC* | 20.0 | |
| Cyclomethicone | 68.0 | |
| Dimethicone | 5.0 | |
| Silica | 2.5 | |
| Water | | 37.85 |

*Aluminium zirconium tetrachlorohydro glycinate

A perfume composition embodying this invention was made and tested for deodorant action in an underarm product, using an Odour Reduction Value test generally as described in U.S. Pat. No. 4,278,658 using the formulator. described in Formulation 3B. The perfume composition and the method for an Odour Reduction Value test are set out below.

| Composition % by weight. | |
|---|---|
| 5 | ACETYL DI ISO AMYLENE |
| 0.3 | ADOXAL |
| 8 | BENZYL ACETATE EXTRA |
| 10 | BENZYL SALICYLATE |

-continued

| Composition % by weight. | |
|---|---|
| 1.5 | CASSIS BASE 345 AB 2967 |
| 1.5 | CITRAL LEMAROME N |
| 12 | CITRONELLOL PURE |
| 3 | CYCLAMEN ALDEHYDE |
| 0.3 | EMPETAL |
| 0.2 | DUPICAL |
| 1.5 | AQUANAL |
| 4.2 | IONONE |
| 8 | LYRAL |
| 1 | METHYL OCTYL ACETALDEHYDE 10% DPG AA 191 |
| 5 | MUGUET NATURE AB 1951 |
| 10 | PHENYL ETHYL ALCOHOL |
| 2 | ROSACETONE |
| 4 | HABANOLIDE |
| 7.5 | TETRAHYDRO LINALOL |
| 15 | METHYL DIHYDRO JASMONATE |

The Odour Reduction Value test was carried out using a panel of 40 Caucasian male subjects. A standard quantity (approximately 0.25 g) of a roll-on product containing one of the perfume compositions or an unperfumed control was applied to the axillae of the panel members in accordance with a statistical design.

After a period of five hours the axiliary odour was judged by three trained female assessors who scored the odour intensity on the 0 to 5 scale, as shown below

| Score | Odour level | Conc. of aqueous isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very Strong | 3.57 |

Average scores for each test product and the control product were then determined and the score for each test product was subtracted from the score for the control product to give the Odour Reduction Value.

The perfume composition described above contained 60.2% of active perfume components and was particularly effective in the Odour Reduction Value test.

What is claimed is:

1. A method for reducing or preventing body malodour by topically applying to human skin a composition comprising an active agent capable of inhibiting the production of odoriferous steroids by micro-organisms on the skin surface, wherein the agent is a perfume composition which is capable of inhibiting bacterial 4-ene reductase and/or 5∞-reductase and which comprises at least 30% by weight of at least 5 perfume components selected from the group consisting of (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, 2-(methyloxy)-4-propyl-1-benzenol, 4-(4-methyl-3-pentenyl)cyclohex-3-ene-1-carbaldehyde, 3-(4-methyl-3-pentenyl)cyclohex-3-ene-1-carbaldehyde, 3-(1,3-benzodioxol-5-yl)-2-methyl-propanal, α-ionone, β-ionone, 4-(4-hydroxy-4-methylpentyl)cyclohex-3-enecarbaldehyde, 3-(4-hydroxy-4-methylpentyl)-cyclohex-3-ene carbaldehyde, methyl iso-eugenol, tetrahydrolinalol, coriander, benzyl salicylate, dupical, phenyl ethyl alcohol, 9-decenol, clove leaf oil distilled, citral and vanillin.

2. A method according to claim 1 wherein an Odour Reduction Value of at least 10% is obtained.

3. A method of producing a perfume composition which comprises (i) evaluating perfume components on the ability to inhibit bacterial 4-ene reductase and/or 5α-reductase, (ii) selecting perfume components on the ability to inhibit bacterial 4-ene reductase and/or 5α-reductase, and (iii) mixing together five or more of said selected perfume components selected from the group consisting of (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, 2-(methyloxy)-4-propyl-1-benzenol, 4-(4-methyl-3-pentenyl)cyclohex-3-ene-1-carbaldehyde, 3-(4-methyl-3-pentenyl)cyclohex-3-ene-1-carbaldehyde, 3-(1,3-benzodioxol-5-yl)-2-methyl-propanal, α-ionone, β-ionone, 4-(4-hydroxy-4-methylpentyl)cyclohex-3-ene-carbaldehyde, 3-(4-hydroxy-4-methylpentyl)cyclohex-3-ene-carbaldehyde, methyl iso-eugenol, tetrahydrolinalol, coriander, benzyl salicylate, dupical, phenyl ethyl alcohol, 9-decenol, clove leaf oil distilled, citral and vanillin to provide a perfume composition comprising at least 30% by weight of said mixed perfume components.

4. A perfume composition comprising at least 60% by weight of at least 5 perfume components, selected from the group consisting of (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, (2-(methyloxy)-4-propyl-1-benzenol), 4-(4-methyl-3-pentenyl)cyclohex-3-ene-1-carbaldehyde, 3-(4-methyl-3-pentenyl)cyclohex-3-ene-1-carbaldehyde, 3-(1,3-benzodioxol-5-yl)-2-methyl-propanal, α-ionone, β-ionone, 4-(4-hydroxy-4-methylpentyl)cyclohex-3-enecarbaldehyde, 3-(4-hydroxy-4-methylpentyl)-cyclohex-3-ene carbaldehyde, methyl iso-eugenol, tetrahydrolinalol, coriander, benzyl salicylate, dupical, phenyl ethyl alcohol, 9-decenol, clove leaf oil distilled, citral, vanillin.

5. A perfume composition comprising at least 30% by weight of at least 5 of the following perfume components, selected from the group consisting of (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, (2-(methyloxy)-4-propyl-1-benzenol), 4-4-methyl-3-pentenyl)cyclohex-3-ene-1-carbaldehyde, 3-(4-methyl-3-pentenyl)cyclohex-3-ene-1-carbaldehyde, 3-(1,3-bensodioxol-5-yl)-2methyl-propanal, α-ionone, β-ionone, 4(4-hydroxy-4-methylpentyl)cyclohex-3-enecarbaldehyde, 3-(4-hydroxy-4-methylpentyl)-cyclohex-3-ene carbaldehyde, methyl iso-eugenot, tetrahydrolinalol, coriander, benzyl salicylate, dupical,phenyl ethyl alcohol, 9-decenol clove leaf oil distilled, citral, vanillin.

6. A deodorant product comprising a perfume composition according to claim 4 or 5.

* * * * *